United States Patent
Aubert et al.

(10) Patent No.: US 8,348,881 B2
(45) Date of Patent: Jan. 8, 2013

(54) DEVICE FOR INJECTING A PHARMACEUTICAL ACTIVE PRINCIPLE

(75) Inventors: Christophe Aubert, Cudrefin (CH); Roland Cherif-Cheikh, Barcelona (ES); Thierry Rimlinger, L'Isle d'Abeau (FR); Fabrice Bonacci, Saint Priest (FR); Serge Barneaud, Puget Theniers (FR)

(73) Assignee: Société de Conseils de Recherches et d'Applications Scientifiques (S.C.R.A.S) SAS, Paris (FR)

( * ) Notice: Subject to any disclaimer, the term of this patent is extended or adjusted under 35 U.S.C. 154(b) by 300 days.

(21) Appl. No.: 11/720,534

(22) PCT Filed: Nov. 15, 2005

(86) PCT No.: PCT/EP2005/012248
§ 371 (c)(1),
(2), (4) Date: May 11, 2009

(87) PCT Pub. No.: WO2006/058614
PCT Pub. Date: Jun. 8, 2006

(65) Prior Publication Data
US 2009/0270797 A1    Oct. 29, 2009

(30) Foreign Application Priority Data
Dec. 1, 2004    (EP) .................................... 04028411

(51) Int. Cl.
*A61M 31/00*    (2006.01)
(52) U.S. Cl. ........................................................ 604/57
(58) Field of Classification Search ................ 604/60, 604/57, 514
See application file for complete search history.

(56) References Cited

U.S. PATENT DOCUMENTS

| | | | |
|---|---|---|---|
| 3,016,895 A | 7/1962 | Sein | |
| 3,809,298 A | 5/1974 | Harris et al. | |
| 4,701,164 A | 10/1987 | Cassou et al. | |
| 4,850,968 A | 7/1989 | Romano | |
| 4,881,551 A | 11/1989 | Taylor | |
| 4,900,303 A * | 2/1990 | Lemelson | 604/514 |
| 4,941,874 A | 7/1990 | Sandow et al. | |

(Continued)

FOREIGN PATENT DOCUMENTS

EP    0 596 162 A1    5/1994

(Continued)

OTHER PUBLICATIONS

International Search Report issued in corresponding application No. PCT/EP2005/012248, completed Jan. 20, 2006 and mailed Jan. 31, 2006.

(Continued)

*Primary Examiner* — Nicholas Lucchesi
*Assistant Examiner* — Diva K Chander
(74) *Attorney, Agent, or Firm* — Griffin & Szipl, P.C.

(57) ABSTRACT

The invention concerns a device for injecting a solid medicine (10) comprising a body (2) inside which moves along a general forward moving axis (X-X) a bevelled (34) needle (4) wherein is introduced the medicine (10), said injection device (1) further comprising retaining means for preventing the medicine from falling (10) prior to being injected. The invention is characterized in that the medicine (10) is retained through an elastic deformation imparted to the needle (4) by the retaining means or by an elastic deformation of the retaining means themselves, or still by the combined flexibility of those two means.

25 Claims, 4 Drawing Sheets

U.S. PATENT DOCUMENTS

| | | | |
|---|---|---|---|
| 4,950,234 A | 8/1990 | Fujioka et al. | |
| 5,019,049 A | 5/1991 | Haining | |
| 5,090,962 A | 2/1992 | Landry et al. | |
| 5,098,402 A | 3/1992 | Davis | |
| 5,141,500 A | 8/1992 | Hake | |
| 5,147,303 A | 9/1992 | Martin | |
| 5,176,643 A | 1/1993 | Kramer et al. | |
| 5,273,541 A | 12/1993 | Malenchek | |
| 5,284,479 A * | 2/1994 | de Jong | 604/60 |
| 5,300,079 A | 4/1994 | Niezink et al. | |
| 5,304,152 A | 4/1994 | Sams | |
| 5,370,620 A | 12/1994 | Shonfeld | |
| 5,522,804 A | 6/1996 | Lynn | |
| 5,542,920 A | 8/1996 | Cherif Cheikh | |
| 5,562,613 A | 10/1996 | Kaldany | |
| 5,632,729 A | 5/1997 | Cai et al. | |
| 5,695,463 A | 12/1997 | Cherif-Cheikh | |
| 5,823,994 A | 10/1998 | Sharkey et al. | |
| 5,984,890 A | 11/1999 | Gast et al. | |
| 6,049,301 A * | 4/2000 | Weagant | 342/13 |
| 6,056,726 A | 5/2000 | Isaacson | |
| 6,179,812 B1 | 1/2001 | Botich et al. | |
| 6,228,049 B1 * | 5/2001 | Schroeder et al. | 604/93.01 |
| 6,402,716 B1 | 6/2002 | Ryoo et al. | |
| 6,478,768 B1 | 11/2002 | Kneer | |
| 6,478,790 B2 | 11/2002 | Bardani | |
| 6,605,073 B1 | 8/2003 | Pressly et al. | |
| 6,752,782 B2 | 6/2004 | Liao | |
| 6,896,670 B2 | 5/2005 | Cherif Cheikh | |
| 6,905,478 B2 | 6/2005 | Ingram et al. | |
| 7,329,235 B2 | 2/2008 | Bertron et al. | |
| 7,500,964 B2 | 3/2009 | Shaw et al. | |
| 7,798,988 B2 * | 9/2010 | Aubert et al. | 604/57 |
| 2002/0161337 A1 | 10/2002 | Shaw et al. | |
| 2002/0193747 A1 | 12/2002 | Denolly | |
| 2003/0004457 A1 | 1/2003 | Andersson | |
| 2003/0040699 A1 | 2/2003 | Talling et al. | |
| 2003/0125669 A1 | 7/2003 | Safabash et al. | |
| 2003/0233101 A1 * | 12/2003 | Lubock et al. | 606/116 |
| 2005/0101967 A1 | 5/2005 | Weber et al. | |
| 2005/0159709 A1 * | 7/2005 | Wilkinson | 604/197 |
| 2008/0249466 A1 * | 10/2008 | Aubert et al. | 604/117 |

FOREIGN PATENT DOCUMENTS

| | | |
|---|---|---|
| EP | 0783342 | 11/1998 |
| EP | 1 666 185 A1 | 7/2006 |

OTHER PUBLICATIONS

Office Action issued in co-pending related U.S. Appl. No. 11/720,542, mailed Aug. 31, 2010.

Notice of Allowance issued on May 26, 2011 in co-pending related U.S. Appl. No. 11/720,542.

* cited by examiner

Prior Art

DEVICE FOR INJECTING A
PHARMACEUTICAL ACTIVE PRINCIPLE

This is a National Phase Application in the United States of International Patent Application No. PCT/EP2005/012248 filed Nov. 15, 2005, which claims priority on European Patent Application No. 04028411.9, filed Dec. 1, 2004. The entire disclosures of the above patent applications are hereby incorporated by reference.

FIELD OF THE INVENTION

The present invention concerns an injection device and, in particular, a device for the intramuscular or subcutaneous injection of an active pharmaceutical principle.

BACKGROUND OF THE INVENTION

In numerous cases, the parenteral administration of active pharmaceutical principles may be preferred to oral absorption, particularly when the medicine to be administered partially or totally decomposes in the digestive system or when a rapid response of the organism is sought.

Parenteral administration of medical principles has, however, certain drawbacks. One of these drawbacks lies in the discomfort experienced by the patient to whom the active principle is being administered. Indeed, parenteral preparations generally take the form of a large volume of liquid in which the medicine is in suspension or dissolved. When the medicine is not very soluble or difficult to pass into suspension, or even when the active principle has to be administered in large doses, a relatively large volume of liquid has to be injected. The ratio between the active principle and the excipient is usually comprised between one percent and one per thousand. The discomfort experienced by the patient thus results both from the size of the needle and the volume of liquid to be injected. In some cases, the very nature of the excipient can also cause the patient suffering.

Another drawback of administering medicine dissolved or in suspension in a liquid medium lies in the fact that the medicine is often unstable in the liquid. The medicine and the liquid must thus be mixed shortly prior to the injection. This can prove particularly disadvantageous when, for example, hundreds of people have to be treated in a small period of time to wipe out an epidemic (administration of a vaccine).

In order to overcome the aforementioned drawbacks, medicines in solid rather than liquid form have been used in order to develop slow release or controlled release preparations. The preparation takes the form of an implant or a rod that is directly injected using a trocar. This type of implant has to enclose the daily dose of medicine multiplied by the number of days of activity, and the quantity of medium sufficient to control the speed of release of the medicine for the time period concerned. Consequently, these solid preparations for injection require a much larger needle than the needles ordinarily used with syringes, which leads to painful injections.

The security injection device disclosed in European Patent No. 0 783 342 overcomes this last drawback. It will be briefly described in conjunction with FIG. 1 annexed to the present Patent Application, which is a cross-section of this type of injection device in the rest position thereof.

Designated as a whole by the general reference numeral 1, the injection device shown in FIG. 1 includes a body 2, which is fixed to a needle 4 via coupling means 6. A rod 8 is driven in translation inside needle 4 and is stopped against a dose 10 of medicinal substance arranged inside said needle 4. A hollow sheath 12 surrounds needle 4 such that the latter is not exposed prior to use. Rod 8 includes a raised portion 14, which limits the travel thereof in body 2. The body 2 includes a collar 16 for facilitating withdrawal of device 1 after injection. A piston 18 is secured to the proximal end of rod 8 and is arranged to slide in a proximal end of body 2. It includes a collar 20. Hollow sheath 12 is placed so as to slide at the distal end of body 2 to enclose needle 4 when it is in the exit position.

The operation of injection device 1 briefly described above is as follows. When the device is pressed against the patient's skin, sheath 12 slides over body 2, thereby exposing needle 4 and allowing the latter to penetrate the skin, while piston 18 and rod 8, arranged as to be able to slide, hold the medicine under the skin when needle 4 is removed.

The solid medicine to be injected is for immediate assimilation by the body. Thus, since the injected quantities are only those necessary to obtain an immediate effect, the needle can be as fine as those of conventional syringes. The injection is less painful insofar as the volume injected is considerably less than the volume necessary for an injection in liquid form. Moreover, the needle of the injection device is not exposed to external elements. Consequently, the needle cannot collect contaminating agents present in the atmosphere or prick anyone inadvertently. Likewise, it is not possible to inadvertently inject a fraction of the medicine or the patient's blood into a member of hospital personnel.

A seal 22 can seal aperture 24 via which needle 4 emerges from injection device 1 in order to preserve the sterility of said needle 4 and the medicinal dose 10. This seal 22 can be made of a brittle material such as biocompatible and biodegradable wax. Alternatively, aperture 24 can be sealed using a cap completely covering sleeve 12.

These means for sealing injection device 1 are not satisfactory. In the case of a wax cap, since there is a non-negligible risk of some of the material remaining caught on the needle and injected into the patient's skin, the manufacturer has to demonstrate the absence of any interaction between the wax and the injected medicine. In the case of a cap, there is a risk of the implant falling at the moment when the said cap is removed.

There therefore existed a need, in the state of the art, for means of preventing the implant falling prior to use of the injection device, particularly during periods of storage and during handling of said injection device prior to carrying out the actual injection.

It is an object of the present invention to answer this need in addition to others by providing an injection device for injecting a solid medicine, including a body inside which there moves a bevelled needle, into which the medicine is introduced, this injection device further including retaining means for preventing the medicine falling prior to injection, characterized in that the medicine is retained via an elastic deformation of the needle imparted by the retaining means or via an elastic deformation of the retaining means themselves, or via a combination of the flexibility of these two means.

SUMMARY OF THE INVENTION

Owing to these features, the present invention provides a device for injecting a solid medicine also called an implant, which can be handled without any excessive precautions without any risk of the implant falling out. In particular, if the open end of the injection device via which the needle exits is sealed with a cap, it is possible, when preparing to carry out the injection, to remove the cap without any fear of the implant falling out. Moreover, since use is made of the elasticity of the needle and/or the retaining means, there is no need to resort to complicated manipulations in order to remove said retaining means before being able to use said device. Moreover, the retaining means do not interfere in any way with the proper operation of the injection device.

According to a complementary feature of the invention, the retaining means temporarily seal the needle bevel in the rest position, thereby preventing the implant from exiting the needle and falling out.

According to a first embodiment of the invention, the retaining means move the aperture through which the needle exits off-centre relative to the general axis of forward movement of said needle inside the injection device.

According to a second embodiment, the retaining means include an elastic tongue that temporarily abuts against the needle bevel.

BRIEF DESCRIPTION OF THE DRAWINGS

Other features and advantages of the present invention will appear more clearly from the following detailed description of two embodiments of the injection device according to the invention, these examples being given purely by way of non-limiting illustration, in conjunction with the annexed drawing, in which.

DETAILED DESCRIPTION OF THE ILLUSTRATIVE EMBODIMENTS

The present invention proceeds from the general inventive idea that consists in fitting a device for injecting a solid medicine also called an implant with means for preventing the medicine falling out during periods of storage or just before the injection is carried out. By employing the elasticity of the needle or their own elasticity, these means do not require the user to resort to complicated manipulations to make said device operational. Moreover, while guaranteeing that the implant will not fall out in the rest position of the needle, the retaining means according to the invention in no way interfere with the exit of the needle and the general proper operation of the injection device.

Figure 1:
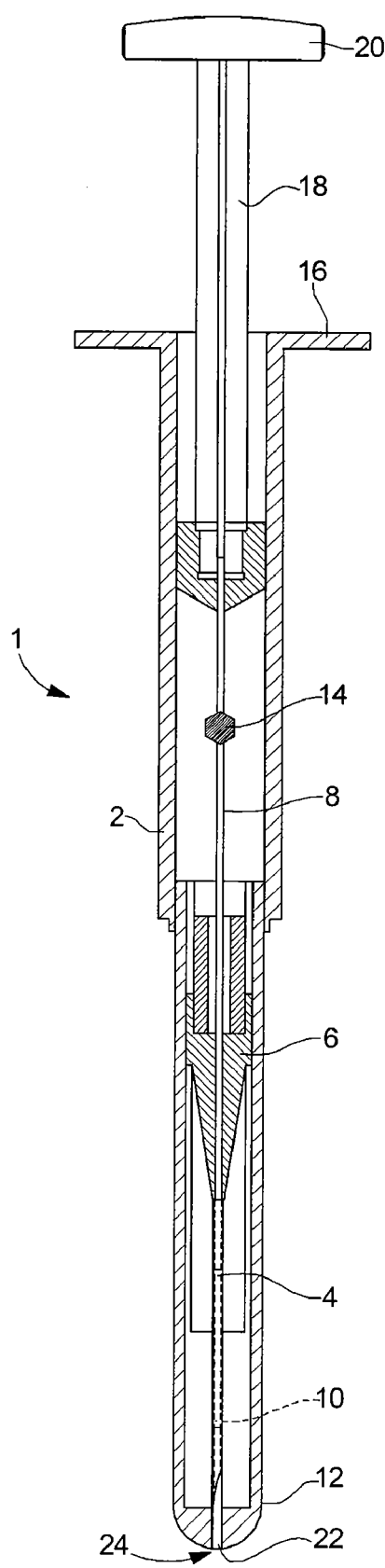
FIG. 1, already mentioned, is a cross-section of a device for injecting a solid medicine.
Figure 2A:
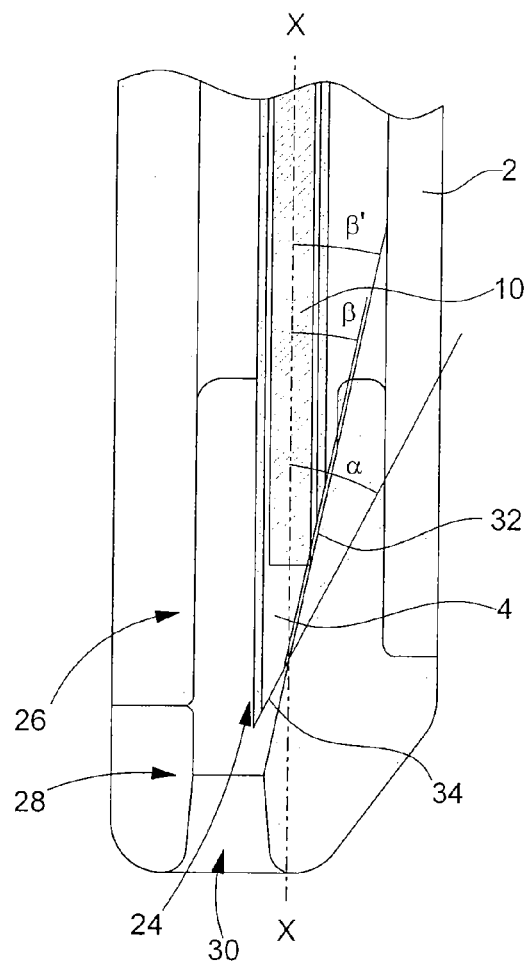
FIGS. 2A and 2B are cross-sections of the distal end of an injection device fitted with means for preventing the medicine falling out according to a first embodiment of the invention, the needle being respectively in the rest position and in the out position.
Figure 2B:
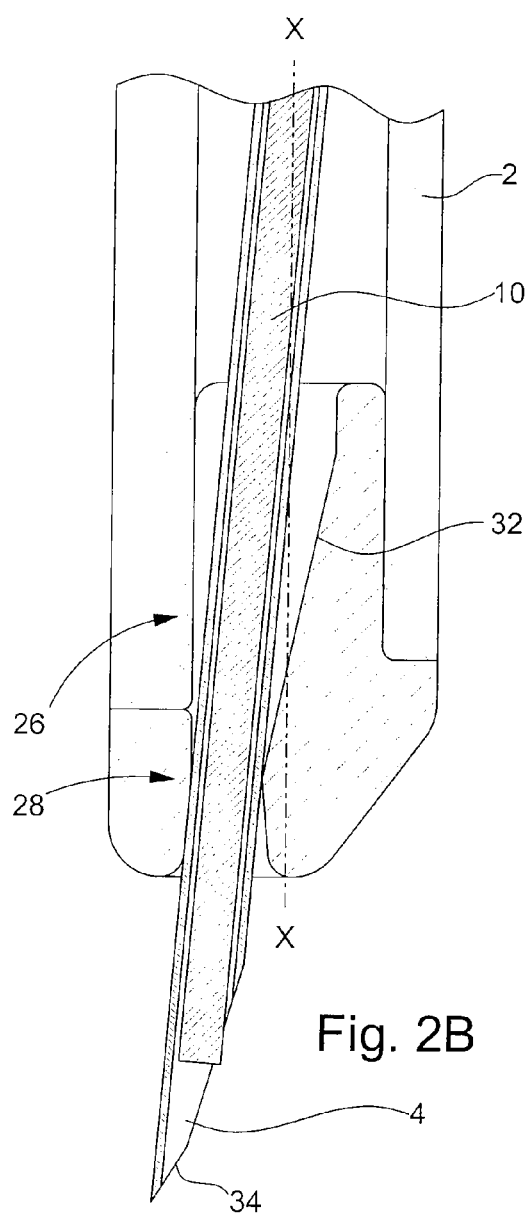

A first embodiment of the retaining means according to the invention is illustrated in FIGS. 2A and 2B. In the following description, the elements that have already been described with reference to FIG. 1 will be designated by the same reference numerals. Injection device 1 described in relation to FIG. 1 is an example given purely by way of non-limiting illustration of the type of injection device to which the present invention could apply.

The distal end 26 of body 2 of the injection device is profiled with an insert 28. This insert 28 is made of a biocompatible plastic material that can be sterilised for example by irradiation, such as a polycarbonate. It is introduced inside body 2 via aperture 24 through which needle 4 exits. Insert 28, of generally cylindrical shape, has an external diameter adapted to the inner diameter of body 2, such that the friction forces between these two parts is sufficient to prevent any risk of said insert 28 inadvertently falling out.

As can be seen upon examining the Figures, insert 28 includes at the base thereof an aperture 30 through which needle 4 exits. This aperture 30 is off-centre relative to the general axis of forward movement X-X of needle 4. Insert 28 thus has, on the face thereof opposite said needle 4, an inclined plane 32, which, from top to bottom, moves closer to the axis of forward movement of said needle 4 until it intercepts the latter and leads to aperture 30. Thus, in the rest position (FIG. 2A), needle 4 abuts via its bevelled aperture 34 against inclined plane 32, which prevents the dose 10 of medicinal substance from falling out. During the exit movement of needle 4 (FIG. 2B), the latter slides over inclined plane 32 by deforming. This movement is made possible owing to the flexibility of needle 4. Bevelled aperture 34, which forms the sharp part of needle 4 is inclined at an angle $\alpha$ relative to axis X-X. This bevelled aperture 34 is preceded by a sliding surface 36 inclined relative to axis X-X at an angle $\beta$ less than angle $\alpha$ via which said needle 4 slides over inclined plane 32. Advantageously, the inclined plane 32 of insert 28 is inclined relative to axis X-X at an angle $\beta'$ substantially equal to angle $\beta$. Consequently, contact is avoided between the sharp part of needle 4 and the inclined plane 32 of insert 28, which could cause a piece of plastic to be torn off.

Figure 3A:
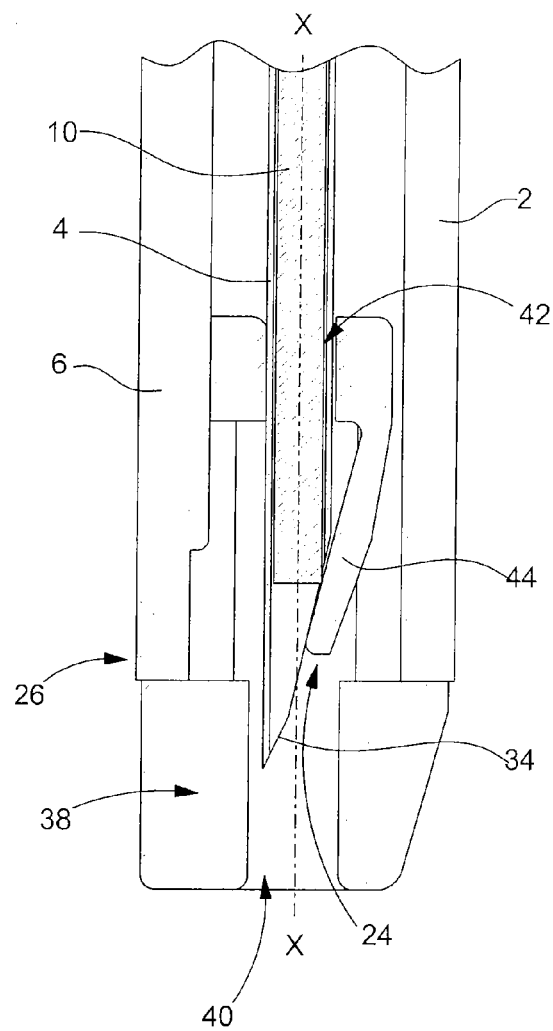
FIGS. 3A and 3B are cross-sections of the distal end of an injection device provided with means for preventing the medicine falling out according to a second embodiment of the invention, the needle being respectively in the rest position and in the out position.
Figure 3B:
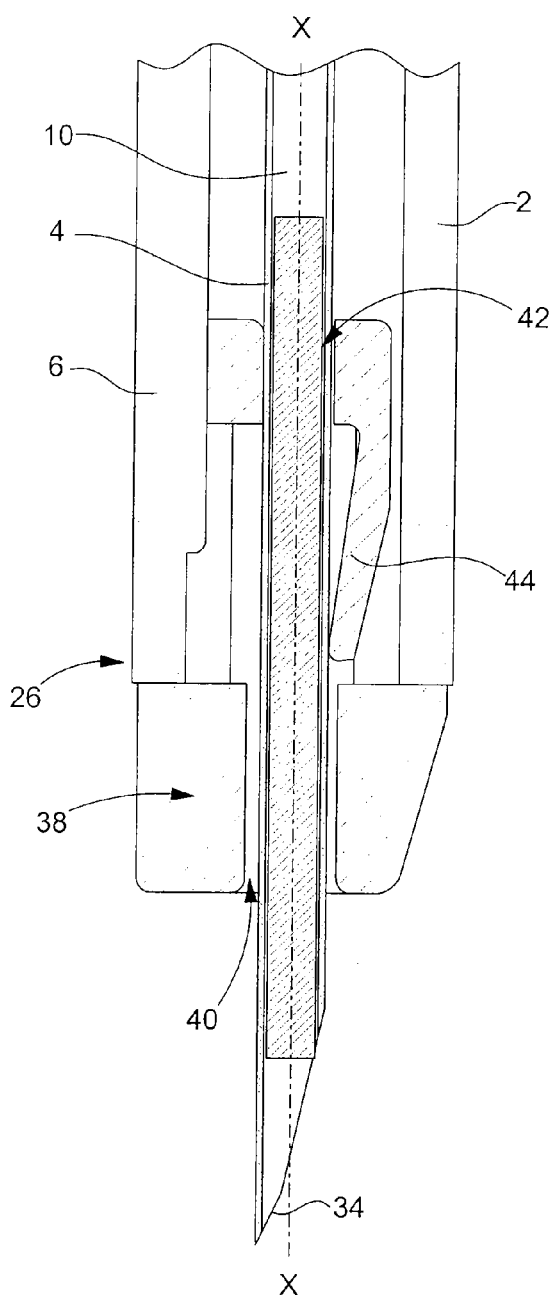

A second embodiment of the retaining means according to the invention is shown in FIGS. 3A and 3B. The distal end 26 of body 2 of the injection device is fitted with an insert 38. As in the preceding case, insert 38 is made of a plastic material such as polycarbonate and is introduced inside body 2 through aperture 24 through which needle 4 exits. Insert 38 is securely retained inside body 2 via the friction forces between said insert 38 and the inner wall of said body 2.

Insert 38 has two through apertures 40 and 42 aligned on the general axis of forward movement X-X of needle 4 inside body 2. The first of these apertures 40 allows needle 4 to exit body 2 of the injection device at the moment that the injection is carried out (see FIG. 3B). The second aperture 42 allows insert 38 to be fitted onto needle 4 at the moment of assembly of said insert 38. During the movement of axial introduction of insert 38 inside body 2, needle 4 moves an elastic tongue 44 away from its rest position. Via the effect of the elastic return force, tongue 44 abuts against the face of the bevelled aperture 34 of said needle 4, preventing dose 10 of medicinal substance from falling out. During the injection, needle 4 moves forward relative to insert 38 and pushes back elastic tongue 44 (see FIG. 3B).

Figures 4A, 4B:
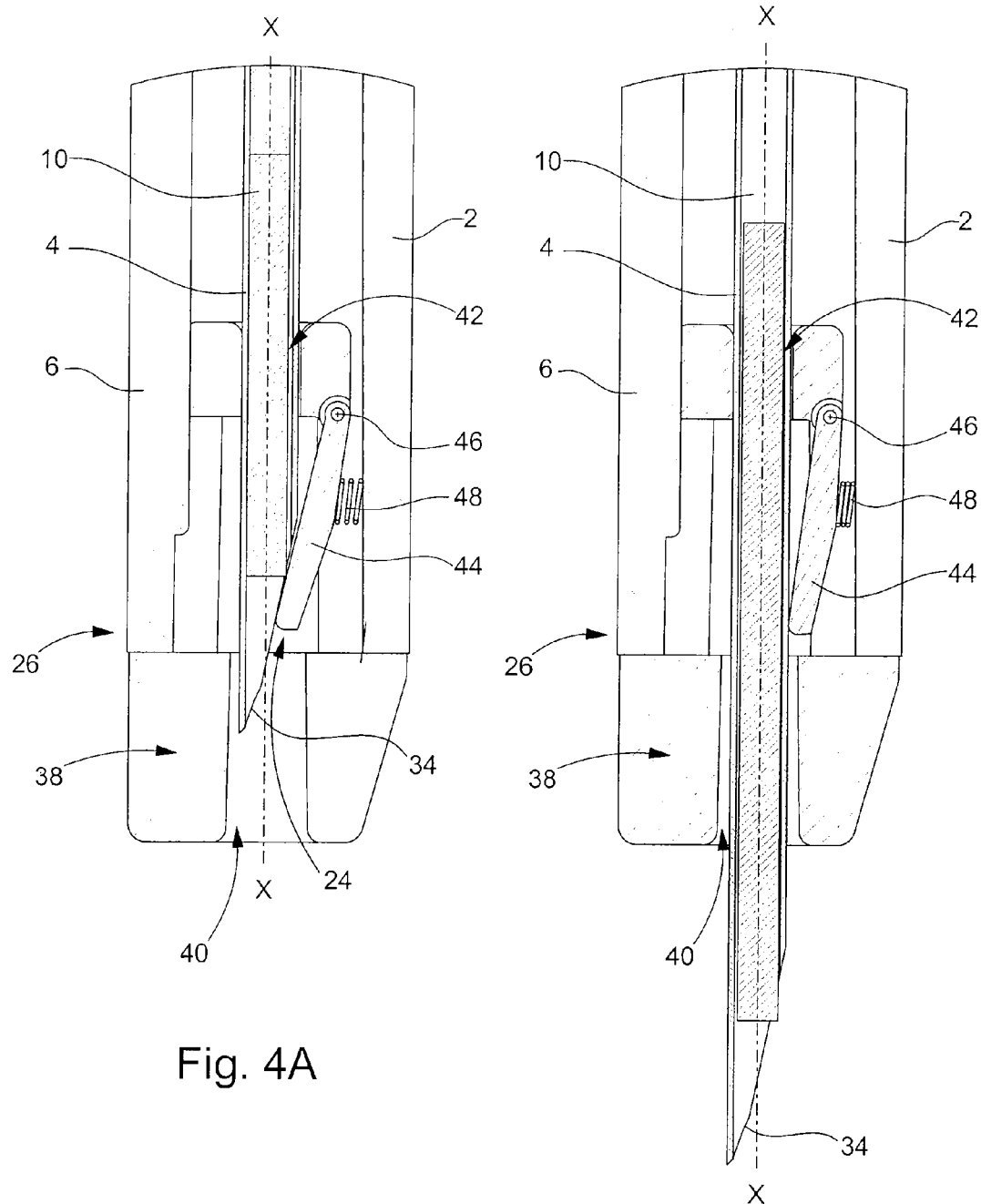
FIGS. 4A and 4B are cross-sections of the distal end of an injection device provided with means for preventing the medicine falling out according to a third embodiment of the invention, the needle being respectively in the rest position and in the out position.

FIGS. 4A and 4B are cross-sections of a variant of the insert 38 described above. Instead of being integral with insert 38, elastic tongue 44 is pivoted on said insert 38 via a hinge 46 and held abutting against the face of the bevelled aperture 34 of needle 4 via the effect of the elastic return force of a spring 48. When needle 4 moves forward, tongue 44 withdraws, which causes spring 48 to compress.

It goes without saying that the present invention is not limited to the embodiments that have just been described and that various simple alterations and variants could be envisaged by those skilled in the art without departing from the scope of the invention as defined by the annexed claims.

The invention claimed is:

1. An injection device for injecting a solid medicine, the injection device including:

(a) a body;
(b) a bevelled needle, disposed inside the body and deformable to inject a medicine, wherein the needle is sufficient to contain the medicine and penetrate the skin of a patient, wherein the needle is operable to move forward along a general axis parallel to the length of the body until exiting out of the body, and to penetrate the skin of a patient and introduce the medicine through the needle thereinto; and
(c) a retaining means, placed on a path of the needle and fixedly mounted inside the body, for preventing the medicine from falling prior to being injected, wherein the needle is deformable relative to the general axis in the injection device when the needle passes the retaining means.

2. The injection device according to claim 1, wherein the retaining means temporarily seal the bevel of the needle, thereby preventing the medicine from exiting the needle and falling.

3. The injection device according to claim 2, wherein the retaining means include an aperture through which the needle exits and which is off-centre relative to the general axis of forward movement of said needle inside the body.

4. The injection device according to claim 1, wherein the retaining means take the form of an insert.

5. An injection device for injecting a solid medicine, the injection device including:
(a) a body;
(b) a bevelled needle disposed inside the body, sufficient to contain a medicine and penetrate the skin of a patient, wherein the needle is operable to move forward along a general axis parallel to the length of the body until exiting out of the body, and to penetrate the skin of a patient and introduce the medicine through the needle thereinto; and
(c) a retaining means, secured to the body and fixedly mounted inside the body, for preventing the medicine from falling prior to being injected, wherein the retaining means include an elastic member that seals the needle when the needle rests and moves away from the needle when the needle moves forward.

6. The injection device according to claim 5, wherein the retaining means temporarily seal the bevel of the needle, thereby preventing the medicine from exiting the needle and falling.

7. The injection device according to claim 3, wherein, opposite the bevel of the needle, the retaining means have an inclined plane which moves closer to the axis of forward movement of said needle until it intercepts the latter and which leads to the aperture.

8. The injection device according to claim 7, wherein the needle has a sliding surface whose inclination is substantially equal to that of the inclined plane.

9. The injection device according to claim 5, wherein the retaining means include an elastic tongue which temporarily abuts against the bevel of the needle.

10. The injection device according to claim 9, wherein, while exiting, the needle pushes back the elastic tongue.

11. The injection device according to claim 10, wherein the elastic tongue is integral with the retaining means.

12. The injection device according to claim 9, wherein the elastic tongue is integral with the retaining means.

13. The injection device according to claim 5, wherein the retaining means take the form of an insert.

14. An injection device for injecting a solid medicine, the injection device including:
(a) a body;
(b) a bevelled needle disposed inside the body, sufficient to contain a medicine and penetrate the skin of a patient, wherein the needle is operable to move forward along a general axis parallel to the length of the body until exiting out of the body, and to penetrate the skin of a patient and introduce the medicine through the needle thereinto; and
(c) a retaining means, secured to the body and fixedly mounted inside the body, for preventing the medicine from falling prior to being injected, wherein the retaining means include an elastic member that seals the needle when the needle rests and moves away from the needle when the needle moves forward, wherein the retaining means temporarily seal the bevel of the needle, thereby preventing the medicine from exiting the needle and falling, and wherein the retaining means include an aperture through which the needle exits and which is off-centre relative to the general axis of forward movement of said needle inside the body.

15. The injection device according to claim 14, wherein, opposite the bevel of the needle, the retaining means have an inclined plane which moves closer to the axis of forward movement of said needle until it intercepts the latter and which leads to the aperture.

16. The injection device according to claim 15, wherein the needle has a sliding surface whose inclination is substantially equal to that of the inclined plane.

17. An injection device for injecting a solid medicine, the injection device including:
(a) a body;
(b) a bevelled needle disposed inside the body, sufficient to contain a medicine and penetrate the skin of a patient, wherein the needle is operable to move forward along a general axis parallel to the length of the body until exiting out of the body, and to penetrate the skin of a patient and introduce the medicine through the needle thereinto; and
(c) a retaining means, secured to the body and fixedly mounted inside the body, for preventing the medicine from falling prior to being injected, wherein the retaining means include an elastic member that seals the needle when the needle rests and moves away from the needle when the needle moves forward, wherein the needle has a sliding surface whose inclination is substantially equal to that of the inclined plane.

18. An injection device for injecting a solid medicine, the injection device including:
(a) a body;
(b) a bevelled needle disposed inside the body, sufficient to contain a medicine and penetrate the skin of a patient, wherein the needle is operable to move forward along a general axis parallel to the length of the body until exiting out of the body, and to penetrate the skin of a patient and introduce the medicine through the needle thereinto; and
(c) a retaining means, secured to the body and fixedly mounted inside the body, for preventing the medicine from falling prior to being injected, wherein the retaining means include an elastic member that seals the needle when the needle rests and moves away from the needle when the needle moves forward, wherein the retaining means include an elastic tongue which temporarily abuts against the bevel of the needle, and wherein the elastic tongue is pivoted on the retaining means via a hinge and is held abutting against the bevel of the needle via the effect of the elastic return force of a spring.

19. An injection device for injecting a solid medicine, the injection device including:
(a) a body;
(b) a bevelled needle disposed inside the body, sufficient to contain a medicine and penetrate the skin of a patient, wherein the needle is operable to move forward along a general axis parallel to the length of the body until exiting out of the body, and to penetrate the skin of a patient and introduce the medicine through the needle thereinto; and
(c) a retaining means, secured to the body and fixedly mounted inside the body, for preventing the medicine from falling prior to being injected, wherein the retaining means include an elastic member that seals the needle when the needle rests and moves away from the needle when the needle moves forward, wherein the retaining means include an elastic tongue which temporarily abuts against the bevel of the needle, wherein, while exiting, the needle pushes back the elastic tongue, and wherein the elastic tongue is pivoted on the retaining means via a hinge and is held abutting against the bevel of the needle via the effect of the elastic return force of a spring.

20. An injection device for injecting a solid medicine, the injection device including:
(a) a body;
(b) a bevelled needle disposed inside the body, sufficient to contain a medicine and penetrate the skin of a patient, wherein the needle is operable to move forward along a general axis parallel to the length of the body until exiting out of the body, and to penetrate the skin of a patient and introduce the medicine through the needle thereinto; and
(c) a retaining means, secured to the body and fixedly mounted inside the body, for preventing the medicine from falling prior to being injected, wherein the retaining means include an elastic member that seals the needle when the needle rests and moves away from the needle when the needle moves forward, wherein the retaining means include an elastic tongue which temporarily abuts against the bevel of the needle, and wherein the retaining means have a first through aperture that allows the needle to exit, and a second through aperture via which said retaining means are fitted onto said needle, said two apertures being aligned on the general axis of forward movement of the needle inside the body.

21. An injection device for injecting a solid medicine, the injection device including:
(a) a body;
(b) a bevelled needle disposed inside the body, sufficient to contain a medicine and penetrate the skin of a patient, wherein the needle is operable to move forward along a general axis parallel to the length of the body until exiting out of the body, and to penetrate the skin of a patient and introduce the medicine through the needle thereinto; and
(c) a retaining means, secured to the body and fixedly mounted inside the body, for preventing the medicine from falling prior to being injected, wherein the retaining means include an elastic member that seals the needle when the needle rests and moves away from the needle when the needle moves forward, wherein the retaining means include an elastic tongue which temporarily abuts against the bevel of the needle, wherein, while exiting, the needle pushes back the elastic tongue, and wherein the retaining means have a first through aperture that allows the needle to exit, and a second through aperture via which said retaining means are fitted onto said needle, said two apertures being aligned on the general axis of forward movement of the needle inside the body.

22. An injection device for injecting a solid medicine, the injection device including:
(a) a body;
(b) a bevelled needle disposed inside the body, sufficient to contain a medicine and penetrate the skin of a patient, wherein the needle is operable to move forward along a general axis parallel to the length of the body until exiting out of the body, and to penetrate the skin of a patient and introduce the medicine through the. needle thereinto; and
(c) a retaining means, secured to the body and fixedly mounted inside the body, for preventing the medicine from falling prior to being injected, wherein the retaining means include an elastic member that seals the needle when the needle rests and moves away from the needle when the needle moves forward, wherein the retaining means include an elastic tongue temporarily abuts against the bevel of the needle, wherein the elastic tongue is integral with the retaining means, and wherein the retaining means have a first through aperture that allows the needle to exit, and a second through aperture via which said retaining means are fitted onto said needle, said two apertures being aligned on the general axis of forward movement of the needle inside the body.

23. An injection device for injecting a solid medicine, the injection device including:
(a) a body;
(b) a bevelled needle, disposed inside the body and deformable to inject a medicine, wherein the needle is sufficient to contain the medicine and penetrate the skin of a patient, wherein the needle is operable to move forward along a general axis parallel to the length of the body until exiting out of the body, and to penetrate the skin of a patient and introduce the medicine through the needle thereinto; and
(c) a retaining means, placed on a path of the needle and fixedly mounted inside the body, for preventing the medicine from falling prior to being injected, wherein the needle is deformable relative to the general axis in the injection device when the needle passes the retaining means, wherein the retaining means take the form of an insert, and wherein the insert is made of a biocompatible material able to be sterilised.

24. The injection device according to claim 23, wherein the insert is made of a plastic material.

25. The injection device according to claim 24, wherein the insert is made of polycarbonate.

* * * * *